United States Patent [19]

Connell et al.

[11] Patent Number: 4,754,032

[45] Date of Patent: Jun. 28, 1988

[54] TRIAZINYLAMINOBENZALDEHYDES

[75] Inventors: David L. Connell, Leeds; John M. Farrar, Bradford, both of Great Britain; Jürg Heller, Oberwil; Hans-Rudolf Schmid, Riehen, both of Switzerland

[73] Assignee: Sandoz Ltd., Basel, Switzerland

[21] Appl. No.: 834,180

[22] Filed: Feb. 26, 1986

[30] Foreign Application Priority Data

Feb. 27, 1985 [GB] United Kingdom ................ 8505064

[51] Int. Cl.⁴ .................. C07D 251/46; C07D 251/52; C07D 251/54
[52] U.S. Cl. ...................................... 544/113; 544/83; 544/197; 544/198; 544/208; 544/209; 544/211; 544/212
[58] Field of Search ................. 544/113, 197, 198, 83, 544/208, 209, 211, 212

[56] References Cited

PUBLICATIONS

March, *Advanced Organic Chemistry*, 2nd ed., 1977, pp. 598–599, 867, 1095, and 1125.

Morrison and Boyd, *Organic Chemistry*, 4th ed., 1983, pp. 872–873.

*Primary Examiner*—Henry R. Jiles
*Assistant Examiner*—Kurt G. Briscoe
*Attorney, Agent, or Firm*—Gerald D. Sharkin; Richard E. Vila; Thomas C. Doyle

[57] ABSTRACT

Compounds of formula I

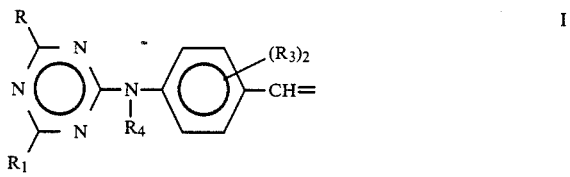

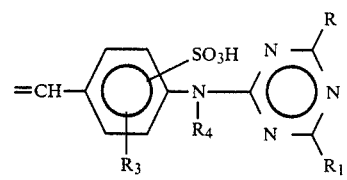

can be used as optical brighteners.

14 Claims, No Drawings

TRIAZINYLAMINOBENZALDEHYDES

The invention relates to a method for preparing asymmetric triazinyl-containing stilbene derivatives.

According to the invention there is provided a process for preparing a compound, in free acid or salt form, of formula I

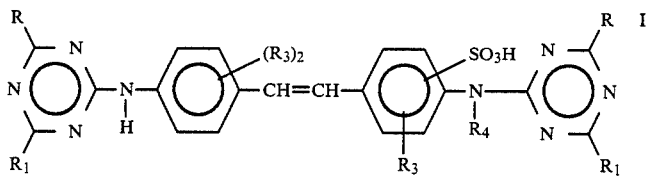

in which R is —NR$_5$R$_6$, —SCH$_3$, halogen or —OR$_5$;
R$_1$ has a significance of R, independent of R;
R$_3$ is hydrogen, methoxy, —COOH; sulphonamido; C$_{1-4}$alkyl; phenylsulphonyl; —CONH$_2$ or —CN;
R$_4$ is hydrogen or methyl;
R$_5$ is hydrogen or phenyl, unsubstituted or substituted by one or two halogen, C$_{1-4}$alkoxy, sulpho, mono- or di-(C$_{1-4}$alkyl)amino or C$_{1-4}$alkyl groups or is C$_{1-4}$alkyl unsubstituted or mono-substituted by hydroxy, C$_{1-4}$alkoxy, cyano or —CONH$_2$;

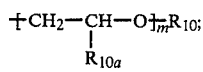

—(CH$_2$)$_p$—CON(R$_{10}$)$_2$; —(CH$_2$)$_p$N(R$_{10}$)$_2$ or —(CH$_2$)$_p$N$^{\oplus}$(R$_{10}$)$_3$ A$^{\ominus}$ where R$_{10}$ is hydrogen or C$_{1-4}$alkyl, m is an integer from 1 to 10 inclusive, p is an integer from 1 to 4 inclusive, R$_{10a}$ is hydrogen or methyl and A$^{\ominus}$ is an anion;
R$_6$ is hydrogen or unsubstituted C$_{1-4}$alkyl or C$_{2-4}$alkyl substituted by one hydroxy, C$_{1-4}$alkoxy, cyano, or —CONH$_2$;

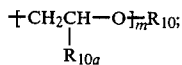

—(CH$_2$)$_p$—CON(R$_{10}$)$_2$; —(CH$_2$)$_p$N(R$_{10}$)$_2$ or —(CH$_2$)$_p$N$^{\oplus}$(R$_{10}$)$_3$A$^{\ominus}$ where R$_{10}$, R$_{10a}$, p, A$^{\ominus}$ and m are as defined above;
or R$_5$ and R$_6$ together with the N-atom to which they are attached form a saturated heterocyclic amine group;
comprising reacting a compound, in free acid or salt form, of formula II

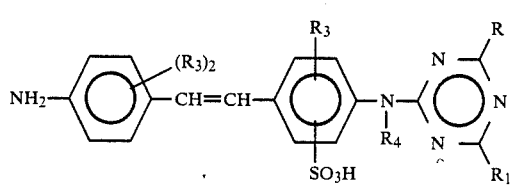

with a compound of formula III

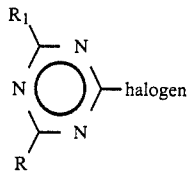

where the symbols are as defined above, and where R and/or R$_1$ is halogen optionally further reacting with H-R$_a$ where R$_a$ is a significance of R other than halogen.

Preferably in a process according to the invention, in the compound of formula I, R is R' and R$_1$ is R$_1$' where R' and R$_1$' are as defined below.

Preferably for the reaction of the compound of formula II with that of formula III, the pH is from 3 to 5 inclusive and the temperature is preferably from −5° to 2° C. inclusive. Where R and/or R$_1$ (in formula III) is halogen and the first (or only) halogen is reacted with H-R$_a$, the pH is preferably from 5.5 to 7 inclusive and the temperature is preferably from 20° to 40° C. Where R and R$_1$ (in formula III) are both halogen and the second halogen group is reacted with H-R$_a$, the pH is preferably 7.5 to 8.5 inclusive and the temperature is preferably 40° to 100° C. inclusive.

In this Specification, unless indicated to the contrary, where a symbol appears more than once in a formula its significances are independent of one another. By the term "halogen" is meant chlorine or bromine preferably chlorine, unless indicated differently. Any substituent that is capable of being linear or branched is linear or branched unless indicated otherwise.

Preferably R is R' where R' is —NH$_2$; —N(R$_6$')$_2$; —NHR$_5$', —SCH$_3$, halogen,

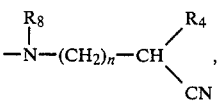

OR$_8$, or a saturated heterocyclic amine group attached to the triazinyl group through the N-atom; where R$_5$' and R$_6$' are defined below and R$_8$ is hydrogen, C$_{1-4}$alkyl or C$_{2-4}$alkyl substituted by —OH or C$_{1-4}$alkoxy and n is 0, 1 or 2. More preferably R is R" where R" is —NH(R$_5$"), —N(R$_6$")$_2$, (where R$_5$" and R$_6$" are defined below) or a saturated heterocyclic amine group attached to the triazinyl group through the N-atom.

Preferably R$_1$ is R$_1$' where R$_1$' has a significance of R', independent of R'; more preferably R$_1$ is R$_1$" where R$_1$" is significance of R" independent of R".

Preferably both groups R and both groups R$_1$ are the same.

Preferably R is not the same as R$_1$ on the same triazinyl group.

Preferably in a process according to the invention, in the compound of formula I, R is R' and R$_1$ is R$_1$' where R' and R$_1$' are as defined above.

More preferably R is

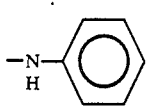

and $R_1$ is more preferably

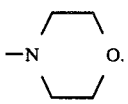

Preferred heterocyclic amine groups are unsubstituted morpholino, unsubstituted piperazinyl; unsubstituted N-methyl piperazinyl; unsubstituted pyrrolidinyl and unsubstituted piperidinyl.

Preferably $R_3$ is $R_3'$ where $R_3'$ is hydrogen or —COOH. More preferably $R_3$ is hydrogen.

Preferably the sulpho group in the stilbene group is ortho to the ethylene group.

Preferably $R_4$ is hydrogen.

Preferably $R_5$ is $R_5'$ where $R_5'$ phenyl, unsubstituted or substituted by one or two halogen, $C_{1-4}$alkoxy, sulpho or $C_{1-4}$alkyl groups or is $C_{1-4}$alkyl, unsubstituted or monosubstituted by one hydroxy, $C_{1-4}$alkoxy or cyano.

More preferably $R_5$ is $R_5''$ where $R_5''$ is phenyl, unsubstituted or substituted by one chloro, methyl, methoxy or sulpho group; or is $C_{1-4}$alkyl or $C_{2-4}$hydroxyalkyl. Most preferably $R_5$ is unsubstituted phenyl.

Preferably $R_6$ is $R_6'$ where $R_6'$ is unsubstituted $C_{1-4}$alkyl or $C_{2-4}$alkyl monosubstituted by $C_{1-4}$alkoxy, cyano or —$CONH_2$ or hydroxy;

More preferably $R_6$ is $R_6''$ where $R_6''$ is $C_{2-4}$alkyl, unsubstituted or monosubstituted by hydroxy.

Preferred salt forms include alkali metal salts, alkaline earth metal salts and ammonium salts.

Further, according to the invention there is provided a process for preparing a compound in free acid or salt form of formula II comprising:

(a) reacting a compound in free acid or salt form of formula IV

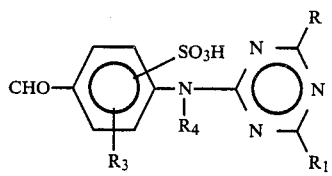

where the symbols are defined above; with a compound of formula V

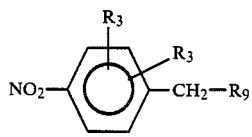

where $R_9$ is

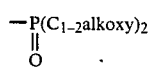

or —H,
to form a compound in free acid or salt form of formula VI

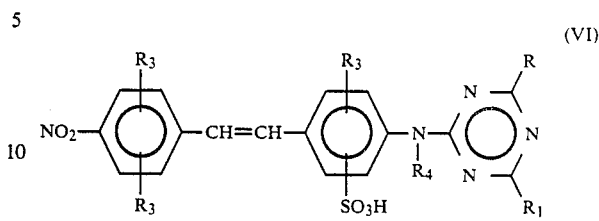

and
(b) reducing the compound of formula VI to form a compound of formula II.

The compounds of formula V where $R_9$ is other than hydrogen can be prepared by reacting a compound of formula VII

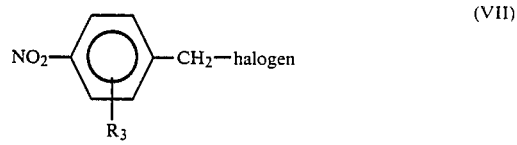

with a compound of formula VIII

Compounds of formula V where $R_9$ is hydrogen are known or may be prepared by known methods from known compounds.

Still further according to the invention there is provided a process for preparing a compound of formula IV comprising oxidising a compound, in free acid or salt form, of formula IX

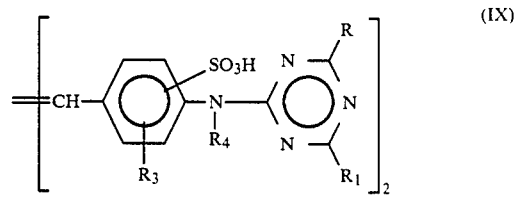

where the symbols are as defined above.

Preferably the pH is from 5 to 8 and preferably the temperature is from 0° to 100° C. Preferably, potassium permanganate is used as oxidizing agent.

Further, according to the invention, there is provided a compound of formula I, defined above in free acid or salt form with the provison that (i) at least one group R is —NH—$R_5$ where $R_5$ is unsubstituted or substituted phenyl; and (ii) if, on one triazinyl group, one of R and $R_1$ is anilino and the other is morpholino and, on the other triazinyl group, one of R and $R_1$ is anilino, the other cannot be morpholino; and (iii) all groups $R_3$ are hydrogen.

Further, according to the invention, there is provided a compound of formula II defined above in free acid or salt form. Preferably all groups $R_3$ are hydrogen. More preferably at least one group R is —NH—$R_5$, where $R_5$ is as defined above.

Further, according to the invention there is provided a compound of formula IV defined above in free acid or salt form.

Preferably in the new compounds of formula I the substituents on the two triazinyl rings are such that the triazinyl rings are not the same.

Compounds of formulae III, VII, VIII and IX are known or can be made from known compounds by known methods.

The compounds of formula I are useful as optical brighteners for addition to detergent compositions and for brightening of textile fabrics and paper. They can be used in the manner disclosed in Example 6 of U.S. Pat. No. 3,895,009, the disclosure of which is incorporated herein by reference.

The invention will now be illustrated by the following Examples in which all temperatures are in °C.

EXAMPLE 1

The compound of formula 1a

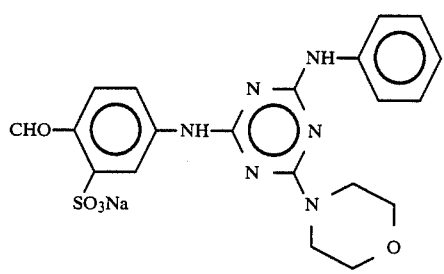

can be prepared as follows:

150 g of KMnO₄ are dissolved in 2 l of water. 965 g of the compound of formula 1b

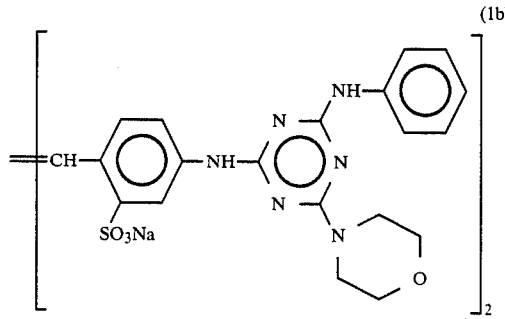

are dissolved in 2.5 l of cellosole and 2.5 l of water. This mixture is cooled to 0° C. and then the KMnO₄ solution is added dropwise whilst maintaining the temperature of the mixture at 0° until a sample of the solution when spotted on filter paper shows a slight pink colour. The mixture is filtered from resultant 1000 g of the compound of formula 1a result which can be recovered by evaporating off the solvent.

EXAMPLE 2

The compound of formula 2a

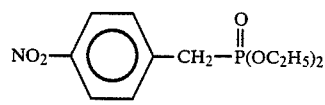

can be prepared by refluxing 791.2 g of nitrobenzyl bromide with 669 g of triethylphosphite in 1000 g of xylene. The ethylbromide resulting is distilled out. 1000 g of the phosphonate of formula 2a results. Excess triethylphosphite and xylene can be removed by heating the mixture under vacuum.

503 g of the compound of formula 2a are mixed with 858.6 g of the compound of formula 1a (defined in Example 1) in 100 g of KOH and 10 liters of dimethylformamide.

The reactants are warmed slowly up to 50° C. and stirred for 3 hours under nitrogen and are poured onto an equal volume of water. The product that results is of formula 2b

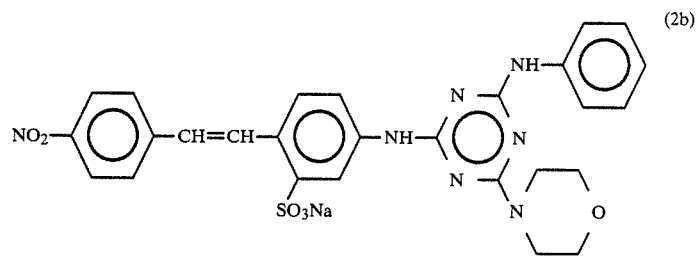

and is filtered off from the solution.

Alternatively, the compound of formula 2b can be prepared as follows:

162.5 g of a wet cake containing the compound of formula 1a (28% actives) are stirred in 75 ml of dimethylformamide and the slurry is made just alkaline with sodium carbonate. The reaction is heated to reflux and 117 ml of water are distilled out. 16.4 g of p-nitrotoluene, 10 ml of piperidine, 10 ml of pyridine and 50 ml of cyclohexane are added. The mixture is heated under azeotropic distillation for 48 hours. Cyclohexane is removed by distillation and the reaction is diluted with water. Pyridine and excess p-nitrotoluene are removed by steam distillation. The reaction is cooled and the orange crystalline product is filtered off. The yield is 35.8 g of the compound of formula 2b (a yield of 60%).

EXAMPLE 3

The compound of formula 3a

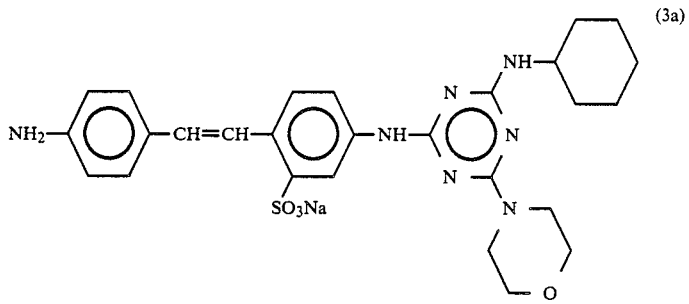

can be prepared as follows:

585 g of iron filings are slurried in 1 l of water and 100 g of acetic acid and this is refluxed for 30 minutes. 1170 g of the compound 2b (defined in Example 2) dissolved in 5 l of dimethyl formamide are added slowly at reflux. The mixture is refluxed for 1 hour and a small amount of caustic soda liquid is added to make the reaction slightly alkaline and the iron is then screened off through "hyflo". The filtrate is concentrated by distillation under vacuum and the amine is filtered off.

Alternatively reduction may be carried out using sodium sulphide.

EXAMPLE 4

The compound of formula 4a

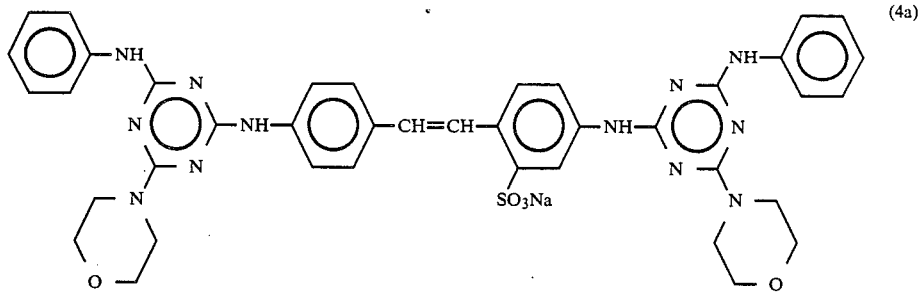

can be prepared as follows:

3449 Parts of methyl ethyl ketone (MEK) in a first vessel are cooled to 0° C. 225 Parts of cyanuric chloride is added whilst stirring until it is fully dissolved in the MEK.

1379 Parts of demineralised water are placed in a second vessel and 1379 parts of a 50% wet cake of the product of formula 3a (defined in Example 3) and isopropanol are added to the water whilst stirring. The resulting slurry is pumped onto the cyanuric chloride solution in the first vessel whilst maintaining the temperature from −2° C. to +2° C. and the pH between 4 and 5 by the addition of 69 parts of sodium bicarbonate portion by portion. When the addition is finished 20 parts of NaOH are added to bring the pH to 6.5.

113 Parts of aniline are added and 180 parts of a 30% sodium hydroxide and 500 parts of water are slowly added to keep the pH between 6.5 and 7. The temperature is allowed to rise. When the reaction is ended and the temperature has risen to 30° C. with the pH at 6.5, 220 parts of morpholine are added and the mixture is heated to 70° C. 12 Parts of sodium hydrosulphite are added to improve the colour. The mixture is refluxed and 333.9 parts of MEK are distilled off. The resulting mass is cooled to 50° C. and filtered and washed. The resulting product is the compound of formula 4a.

EXAMPLES 5 to 11

Compounds of the formula

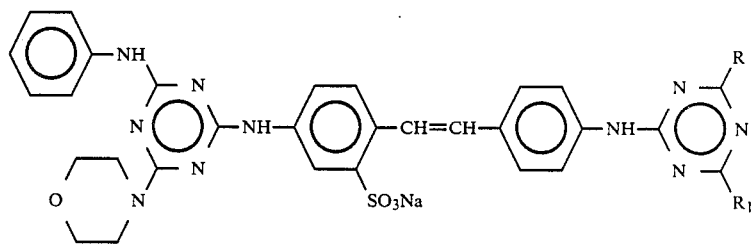

in which the symbols are defined in the Table below, can be made from appropriate reactants by an method analogous to that of Example 4.

TABLE

| Example No. | R | $R_1$ |
|---|---|---|
| 5 | −NH−⟨phenyl⟩−SO₃Na | −N(morpholine)O |

TABLE-continued

| Example No. | R | $R_1$ |
|---|---|---|
| 6 | −NH−⟨phenyl⟩ | −N(CH$_2$CH$_2$OH)$_2$ |
| 7 | −N(CH$_3$)−CH$_2$−CH$_2$−OH | −Cl |
| 8 | −NH−⟨phenyl-SO$_3$Na, SO$_3$Na⟩ | −N(CH$_2$CHOHCH$_3$)$_2$ |
| 9 | −NH−⟨phenyl-Cl⟩ | −NHCH$_2$CH$_2$OCH$_2$CH$_2$OH |
| 10 | −NH−⟨phenyl⟩ | −OCH$_3$ |
| 11 | −N(morpholino) | −N(morpholino) |

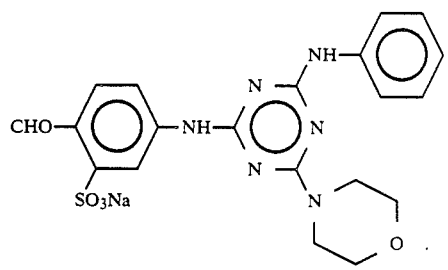

We claim:

1. A compound, in free acid or salt form, of formula IV $$\text{CHO—}\underset{R_3}{\overset{SO_3H}{\bigcirc}}\text{—}\underset{R_4}{N}\text{—}\underset{N}{\overset{R}{\underset{N}{\bigcirc}}}\text{—}R_1 \quad (IV)$$

in which R is −NR$_5$R$_6$, −SCH$_3$, halogen or −OR$_5$
R$_1$ has a significance of R, independent of R;
each R$_3$ independently, is hydrogen, methoxy, −COOH; sulphonamido; C$_{1-4}$alkyl; phenylsulphonyl; −CONH$_2$ or −CN;
R$_4$ is hydrogen or methyl;
each R$_5$, independently, is hydrogen or phenyl, unsubstituted or substituted by one or two halogen, C$_{1-4}$alkoxy, sulpho, mono- or di-(C$_{1-4}$alkyl)-amino or C$_{1-4}$alkyl groups or is C$_{1-4}$alkyl unsubstituted or monosubstituted by hydroxy, C$_{1-4}$alkoxy, cyano or CONH$_2$;

$$\text{—}(CH_2\text{—}\underset{R_{10a}}{CH}\text{—}O)_m R_{10};$$

(CH$_2$)$_p$−CON(R$_{10}$)$_2$; (CH$_2$)$_p$N(R$_{10}$)$_2$ or (CH$_2$)$_p$N$^\oplus$(R$_{10}$)$_3$A$^\ominus$ where R$_{10}$ is hydrogen or C$_{1-4}$alkyl, m is an integer from 1 to 10 inclusive, p is an integer from 1 to 4 inclusive, R$_{10a}$ is hydrogen or methyl and A$^\ominus$ is an anion;
each R$_6$, independently, is hydrogen or unsubstituted C$_{1-4}$alkyl or C$_{2-4}$alkyl, substituted by one hydroxy, C$_{1-4}$alkoxy, cyano or −CONH$_2$;

$$\text{—}(CH_2\text{—}\underset{R_{10a}}{CH}\text{—}O)_m R_{10};$$

−(CH$_2$)$_p$−CON(R$_{10}$)$_2$; (CH$_2$)$_p$N(R$_{10}$)$_2$ or (CH$_2$)$_p$N$^\oplus$(R$_{10}$)$_3$A$^\ominus$;
or R$_5$ and R$_6$ together with the N-atom to which they are attached form an unsubstituted morpholino, unsubstituted piperazinyl, unsubstituted N-methyl piperazinyl, unsubstituted pyrrolidinyl or unsubstituted piperidinyl group.

2. A compound according to claim 1 wherein R is R' where R' is −NH$_2$, −N(R$_6$')$_2$, −NHR$_5$', −SCH$_3$, halogen, $$\text{—}\underset{R_8}{N}\text{—}(CH_2)_n\text{—}CH\underset{CN}{\overset{R_4}{\diagdown}},$$

OR$_8$, or a saturated heterocyclic amine group attached to the triazinyl group through the N-atom and selected from the group consisting of unsubstituted morpholino, unsubstituted piperazinyl, unsubstituted N-methyl piperazinyl, unsubstituted pyrrolidinyl and unsubstituted piperidinyl,
R$_1$ is R$_1$' where R$_1$' has a significance of R' independent of R',
R$_5$' is phenyl, unsubstituted or substituted by one or two halogen, C$_{1-4}$alkoxy, sulpho or C$_{1-4}$alkyl groups or is C$_{1-4}$alkyl unsubstituted or monosubstituted by hydroxy, C$_{1-4}$alkoxy or cyano,
R$_6$' is unsubstituted C$_{1-4}$alkyl or C$_{2-4}$alkyl monosubstituted by C$_{1-4}$alkoxy, cyano, −CONH$_2$ or hydroxy,
R$_8$ is hydrogen, C$_{1-4}$alkyl or C$_{2-4}$alkyl substituted by −OH or C$_{1-4}$alkoxy, and
n is 0, 1 or 2.

3. A compound according to claim 1 wherein R is R'' where R'' is −NHR$_5$'', −N(R$_6$'')$_2$ or a saturated heterocyclic amine group attached to the triazinyl group through the N-atom and selected from the group consisting of unsubstituted morpholino, unsubstituted piperazinyl, unsubstituted N-methyl piperazinyl, unsubstituted pyrrolidinyl and unsubstituted piperidinyl,
R$_1$ is R$_1$'' where R$_1$'' is a significance of R'' independent of R'',
R$_5$'' is phenyl, unsubstituted or substituted by one chloro, methyl, methoxy or sulpho group, or is C$_{1-4}$alkyl or C$_{2-4}$hydroxyalkyl, and
R$_6$'' is C$_{2-4}$alkyl, unsubstituted or monosubstituted by hydroxy.

4. A compound according to claim 1 wherein R is not the same as R$_1$.

5. A compound according to claim 1 wherein R$_3$ is R$_3$' where R$_3$ is hydrogen or −COOH.

6. A compound according to claim 2 wherein R' is not the same as R$_1$'.

7. A compound according to claim 2 wherein R$_3$ is R$_3$' where R$_3$' is hydrogen or −COOH.

8. A compound according to claim 3 wherein R" is not the same as $R_1''$

9. A compound according to claim 3 wherein $R_3$ is hydrogen.

10. A compound according to claim 6 wherein $R_3$ is $R_3'$ where $R_3'$ is hydrogen or —COOH.

11. A compound according to claim 8 wherein $R_3$ is hydrogen.

12. A compound according to claim 10 wherein $R_4$ is hydrogen.

13. A compound according to claim 11 wherein $R_4$ is hydrogen.

14. The compound according to claim 13 of the formula